(12) United States Patent
Desiderio et al.

(10) Patent No.: US 8,530,180 B2
(45) Date of Patent: Sep. 10, 2013

(54) METHOD FOR IDENTIFYING SMOKER OR EX-SMOKER AT RISK OF CHRONIC OBSTRUCTIVE PULMONARY DISEASE

(75) Inventors: Dominic M. Desiderio, Memphis, TN (US); Xianquan Zhan, Memphis, TN (US)

(73) Assignee: Chiesi Farmaceutici S.p.A., Parma (IT)

( * ) Notice: Subject to any disclaimer, the term of this patent is extended or adjusted under 35 U.S.C. 154(b) by 678 days.

(21) Appl. No.: 12/648,964

(22) Filed: Dec. 29, 2009

(65) Prior Publication Data

US 2010/0183578 A1  Jul. 22, 2010

Related U.S. Application Data

(60) Provisional application No. 61/141,492, filed on Dec. 30, 2008.

(51) Int. Cl.
*C12Q 1/37* (2006.01)
*C12P 21/06* (2006.01)

(52) U.S. Cl.
USPC .......................................... 435/23; 435/68.1

(58) Field of Classification Search
None
See application file for complete search history.

(56) References Cited

U.S. PATENT DOCUMENTS

| | | | | |
|---|---|---|---|---|
| 5,905,032 | A | * | 5/1999 | Walton et al. .............. 435/173.2 |
| 7,972,795 | B2 | * | 7/2011 | Thorin et al. .................. 435/7.1 |
| 2005/0187268 | A1 | * | 8/2005 | von Rechenberg et al. .. 514/362 |
| 2006/0177830 | A1 | * | 8/2006 | Pasha et al. ........................ 435/6 |
| 2007/0224287 | A1 | * | 9/2007 | Wright et al. ................. 424/617 |
| 2009/0048150 | A1 | * | 2/2009 | Ischiropoulos ................... 514/2 |

* cited by examiner

*Primary Examiner* — David M Naff
(74) *Attorney, Agent, or Firm* — Oblon, Spivak, McClelland, Maier & Neustadt, L.L.P.

(57) ABSTRACT

Specific nitroprotein biomarkers may be used as prognostic and diagnostic tools for COPD. Identification of certain specific nitroprotein biomarkers allows the development of targeted therapies aimed at prevention and treatment of COPD.

9 Claims, No Drawings

SEQUENCE LISTING

<160> NUMBER OF SEQ ID NOS: 10

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Optionally nitrated Tyr

<400> SEQUENCE: 1

Leu Tyr Thr Tyr Glu Gln Ile Pro Gly Ser Leu Lys Asp Asn Pro Tyr
1               5                   10                  15

Ile Thr Asp Gly Tyr Arg Ala Tyr Leu Pro Ser Arg
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Optionally nitrated Tyr

<400> SEQUENCE: 2

Asp Leu Tyr Arg Asp Val Met Leu Glu Ile Tyr Ser Asn Leu Leu Ser
1               5                   10                  15

Met Gly Tyr Gln Val Ser Lys Pro Asp Ala Leu Ser Lys
            20                  25

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Optionally nitrated Tyr

<400> SEQUENCE: 3

Asp Tyr Leu Ala Ala Ile Ala
1               5

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Optionally nitrated Tyr
<220> FEATURE:
<221> NAME/KEY: MOD_RES
<222> LOCATION: (7)..(7)
<223> OTHER INFORMATION: Optionally nitrated Tyr

```
<220> FEATURE:
<221> NAME/KEY: MOD_RES
<222> LOCATION: (18)..(18)
<223> OTHER INFORMATION: Optionally deaminated Gln

<400> SEQUENCE: 4

Glu Leu Tyr Arg Ala Trp Tyr Arg Glu Val Pro Asn Thr Val His Gln
1               5                   10                  15

Phe Gln Leu Asp Ile Thr Val Lys
            20

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Optionally deaminated Asn
<220> FEATURE:
<221> NAME/KEY: MOD_RES
<222> LOCATION: (24)..(24)
<223> OTHER INFORMATION: Optionally nitrated Tyr

<400> SEQUENCE: 5

His Asp Cys Val Asn Gly Gly Val Cys Val Asp Gly Ile Gly Asn Tyr
1               5                   10                  15

Thr Cys Gln Cys Pro Leu Gln Tyr Thr Gly Arg
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Optionally deaminated Asn
<220> FEATURE:
<221> NAME/KEY: MOD_RES
<222> LOCATION: (17)..(17)
<223> OTHER INFORMATION: Optionally nitrated Tyr
<220> FEATURE:
<221> NAME/KEY: MOD_RES
<222> LOCATION: (26)..(26)
<223> OTHER INFORMATION: Optionally deaminated Asn

<400> SEQUENCE: 6

Asn Lys Asn Gly Ser Thr Asp Tyr Gly Ile Phe Gln Ile Asn Asn Lys
1               5                   10                  15

Tyr Trp Cys Asp Ser Gly Tyr Gly Ser Asn Asp Cys Lys
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Optionally nitrated Tyr
```

```
<220> FEATURE:
<221> NAME/KEY: MOD_RES
<222> LOCATION: (17)..(17)
<223> OTHER INFORMATION: Optionally deaminated Asn
<220> FEATURE:
<221> NAME/KEY: MOD_RES
<222> LOCATION: (23)..(23)
<223> OTHER INFORMATION: Optionally deaminated Asn

<400> SEQUENCE: 7

Phe Ser Leu Asp Gly Lys Thr Tyr Asn Leu Glu Lys Asn Asn Gly Pro
1               5                   10                  15

Asn Ser Leu His Ser Gly Asn Pro Gly Phe Asp Lys
            20                  25

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Optionally nitrated Tyr
<220> FEATURE:
<221> NAME/KEY: MOD_RES
<222> LOCATION: (14)..(14)
<223> OTHER INFORMATION: Optionally nitrated Tyr
<220> FEATURE:
<221> NAME/KEY: MOD_RES
<222> LOCATION: (19)..(19)
<223> OTHER INFORMATION: Optionally deaminated Gln

<400> SEQUENCE: 8

Glu Tyr Gln Leu Ile Leu Ala Pro Gln Val Ala Ser Asn Tyr Glu Asp
1               5                   10                  15

Ile Lys Gln Asp Thr Asp Arg
            20

<210> SEQ ID NO 9
<211> LENGTH: 8
<212> TYPE: PRT
<213> ORGANISM: Unknown
<220> FEATURE:
<223> OTHER INFORMATION: Description of Unknown Sequence: Lysozyme
      tyrosine kinase phosphorylation motif

<400> SEQUENCE: 9

Lys Tyr Trp Cys Asp Ser Gly Tyr
1               5

<210> SEQ ID NO 10
<211> LENGTH: 9
<212> TYPE: PRT
<213> ORGANISM: Acetinobacter baumannii

<400> SEQUENCE: 10

Lys Phe Ser Leu Asp Gly Lys Thr Tyr
1               5
```

METHOD FOR IDENTIFYING SMOKER OR EX-SMOKER AT RISK OF CHRONIC OBSTRUCTIVE PULMONARY DISEASE

CROSS REFERENCES TO RELATED APPLICATIONS

This application claims priority to U.S. Provisional Patent Application No. 61/141,492, filed on Dec. 30, 2008, which is incorporated herein by reference in its entirety.

BACKGROUND OF THE INVENTION

1. Field of the Invention

The present invention relates to novel nitroprotein markers for lung damage caused by smoke exposure, and to methods identifying people vulnerable to developing Chronic Obstructive Pulmonary Disease (COPD) and related respiratory conditions using such a marker. The present invention also relates to therapeutic methods for targeting such a nitroprotein to prevent and treat respiratory disease.

2. Discussion of the Background

Chronic Obstructive Pulmonary Disease (COPD) is a disease of the lungs in which the airways become narrowed and the patient experiences shortness of breath. The limitation of airflow is poorly reversible and usually worsens over time.

The prevalence and associated mortality of COPD have increased dramatically in recent years, due in large part to cigarette smoking. It is projected to be the third leading cause of death worldwide by 2020. Noxious particles in smoke trigger an inflammatory response in the lung, leading to destruction of alveolar tissue, a condition known as emphysema. The inflammatory response in the larger airways is known as chronic bronchitis, which is diagnosed clinically when sputum is coughed up.

Cigarette smoke is a complex mixture of substances including oxidants and nitrosants such as nitric oxide that may initiate the inflammatory response in the lung. Alveolar macrophages, neutrophils, CD8+ lymphocytes, other inflammatory cells and airway epithelial cells generate and release reactive oxygen species (ROS) such as the superoxide anion ($O_2^-$), hydrogen peroxide ($H_2O_2$), and the hydroxyl radical ($OH^-$) through an NADPH-oxidase-dependent mechanism. These cells can also generate nitric oxide ($NO^-$) free radical through a nitric oxide synthase (NOS)-dependent mechanism. Inducible NOS (iNOS) can generate large amounts of NO for an extended period of time during an inflammatory response. Most of the cellular toxic effects of NO result from its rapid reaction with $O_2^-$ to form the strong nitrosant peroxynitrite anion ($ONOO^-$). Peroxynitrite causes the nitration (addition of $-NO_2$) of a protein tyrosine residue. Tyrosine nitration can compromise protein structure and function, the impact mainly being on the structural and conformation properties of proteins and their potential signalling and catalytic activities.

Detection and quantification of total nitrotyrosine in biological samples has been conducted using anti-nitrotyrosine antibodies and by HPLC. The results have confirmed that smokers have higher degrees of protein nitration than non-smokers (Zhang W Z et al. Biomed. Chromatogr., 2007, 21(3): 273-8), and that tyrosine nitration is considerably increased in the lung tissue of patients with ARDS (adult respiratory distress syndrome) relative to non-ARDS controls (Haddad et al. J. Clin. Invest., 94: 2407-2413, 1994).

The prior art does not describe any analysis of individual protein nitration in lung disease, nor diagnostic measures for COPD dependent on selectively detecting and analysing individual nitroproteins or nitropeptides in a biological sample.

Currently COPD is diagnosed by lung function tests such as spirometry, or procedures such as blood tests, chest X-rays and Computed Tomography (CT) scans.

To a certain degree the condition can be controlled by lifestyle changes such as cessation of smoking, nutrition, exercise and avoidance of air pollution. However, to date there are no pharmacologic therapies that can reduce the decline in lung function that characterizes COPD, although the symptoms can be managed with systemic corticosteroids and bronchodilators.

Part of the difficulty in developing treatments for COPD is that although there are many candidate COPD biomarkers (e.g. sputum neutrophils, interleukin (IL)-8, and tumor necrosis factor-α), there is a lack of validated lung-specific biomarkers that can be used as an intermediate end point for clinical trials. Biomarkers can be defined as indicators associated with a particular disease or condition where there is a correlation between the presence or level of the biomarker and some aspect of the disease or condition. One important criterion for a COPD biomarker is that it should have biological plausibility in terms of its role in pathogenesis of the disease. Recently, C-reactive Protein (CRP) was proposed as blood-based marker for COPD, but it has since been discredited because it is a general, rather than lung-specific marker for systemic inflammation (Sin and Man, Chest, 2008; 133; 1296-1298).

Thus, there is an urgent need to identify new, preferably lung-specific biomarkers that can allow physicians to monitor the stage of advancement of COPD and its associated underlying physiological changes.

SUMMARY OF THE INVENTION

Accordingly, it is one object of the present invention to provide novel methods for identifying a patient at risk of developing COPD.

It is another object of the present invention to provide novel methods for diagnosing early stage COPD in a patient.

It is another object of the present invention to provide novel methods for monitoring the progression of COPD in a patient.

It is another object of the present invention to provide novel methods for assessing the efficacy of a potential therapeutic agent for COPD.

It is another object of the present invention to provide novel methods for assessing the harmful potential of a substance in causing COPD.

It is another object of the present invention to provide novel ligands capable of specifically and selectively binding to individual nitroproteins or nitropeptides, and their use in therapeutic treatment of COPD.

It is another object of the present invention to provide novel antibodies and their use in the manufacture of a medicament for the prevention or treatment of COPD It is another object of the present invention to provide novel diagnostic kits for identifying individuals susceptible to developing COPD.

It is another object of the present invention to provide novel pharmaceutical compositions comprising such a ligand.

It is another object of the present invention to provide novel pharmaceutical vaccine compositions for COPD.

These and other objects, which will become apparent during the following detailed description, have been achieved by the inventors' discovery that certain nitroproteins or nitropeptides are markers for COPD.

Thus, the present invention provides:

(1) A method for identifying a patient at risk of developing COPD, comprising the steps of:
   (i) obtaining a biological sample from a patient;
   (ii) selectively identifying the presence or absence of one or more individual nitroproteins in the sample; and
   (iii) identifying the patient as being at risk of developing COPD if one or more said nitroproteins is present in the sample.

(2) A method for diagnosing early stage COPD in a patient, comprising the steps of:
   (i) obtaining a biological sample from a patient;
   (ii) selectively identifying the presence or absence of one or more individual nitroproteins in the sample; and
   (iii) identifying the patient as having early stage COPD if one or more said nitroproteins is present in the sample.

(3) A method for monitoring the progression of COPD in a patient, comprising the steps of:
   (i) obtaining a first biological sample from a patient;
   (ii) selectively identifying the presence or absence of one or more individual nitroproteins in the first sample, and optionally quantifying them;
   (iii) obtaining a second biological sample from the patient at a later time point;
   (iv) selectively identifying the presence or absence of said one or more individual nitroproteins in the second sample, and optionally quantifying them; and
   (v) diagnosing a progression in COPD in the patient if there is a significant increase in the number or quantities of any individual nitroproteins in the second sample relative to the first sample.

(4) The use of individual nitroproteins or nitropeptides as biomarkers for COPD.

(5) The use of a nitroprotein or nitropeptide in the diagnosis of COPD and precursor conditions, wherein the nitroprotein or nitropeptide is selected from the group of nitrated proteins consisting of progestin and adipoQ receptor family member III, zinc finger protein 432, proteasome subunit alpha type 2, NADH-ubiquinone oxidoreductase B14, slit homolog 1 protein, lysozyme, and peptide fragments thereof.

(6) A method for assessing the efficacy of a potential therapeutic agent for COPD in a subject who has been diagnosed with COPD, comprising the steps of:
   (i) obtaining a first biological sample from the subject before administering the potential therapeutic agent;
   (ii) then administering the potential therapeutic agent to the subject;
   (iii) obtaining a second biological sample from the subject after administering the potential therapeutic agent;
   (iv) selectively identifying the presence or absence of one or more individual nitroproteins in the first and in the second sample, and optionally quantifying them; and
   (v) confirming the efficacy of the potential therapeutic agent in the patient if there is a significant decrease in the number or quantities of any individual nitroproteins in the second sample relative to the first sample.

(7) A method for assessing the harmful potential of a substance in causing COPD, comprising the steps of:
   (i) obtaining a first biological sample from an animal before administering the substance;
   (ii) then administering the potentially harmful substance to the animal;
   (iii) obtaining a second biological sample from the animal after administering the substance;
   (iv) selectively identifying the presence or absence of one or more individual nitroproteins in the first and in the second sample, and optionally quantifying them; and
   (v) confirming the harmful effect of the substance in the patient if there is a significant increase in the number or quantities of any individual nitroproteins in the second sample relative to the first sample.

(8) A ligand capable of specifically and selectively binding to individual nitroproteins or nitropeptides, and their use in therapeutic treatment of COPD.

(9) An antibodies and their use in the manufacture of a medicament for the prevention or treatment of COPD, wherein the antibodies specifically recognise a protein selected from the group consisting of progestin and adipoQ receptor family member III, zinc finger protein 432, proteasome subunit alpha type 2, NADH-ubiquinone oxidoreductase B14, slit homolog 1 protein, and lysozyme. Preferably the antibodies selectively recognise the protein in its nitrated form.

(10) A diagnostic kit for identifying individuals susceptible to developing COPD, comprising antibodies capable of specifically recognising and binding to nitroproteins or nitropeptides from a biological sample, said proteins being selected from the group consisting of progestin and adipoQ receptor family member III, zinc finger protein 432, proteasome subunit alpha type 2, NADH-ubiquinone oxidoreductase B14, slit homolog 1 protein, and lysozyme.

(11) A pharmaceutical composition comprising a ligand capable of binding to the nitroproteins or nitropeptides of the invention, and one or more pharmaceutically acceptable excipients.

(12) A pharmaceutical vaccine composition comprising a nitroprotein or nitropeptide, and one or more pharmaceutically acceptable excipients, and optionally one or more adjuvants. Preferably the nitropeptide is selected from the group consisting of SEQ IDs NO:1-5. Also provided is the use of such a vaccine composition for vaccinating a human to prevent or treat COPD.

Now, for the first time, individual nitroproteins in bronchoalveolar lavage fluid (BALF) from ex-smokers have been characterized in detail, using pioneering techniques from the emerging field of nitroproteomics. The presence of these nitroproteins may be predictive of development of lung conditions such as COPD. A number of the identified nitroproteins are known to perform critical roles in preserving lung function in their non-nitrated form, and their nitration as a result of smoking-related lung damage is strongly suggestive of their potential as targets in therapies aiming to prevent and reverse lung damage in smokers, ex-smokers and passive smokers.

DETAILED DESCRIPTION OF THE PREFERRED EMBODIMENTS

Identification and optional quantification of individual nitroproteins or nitropeptides in biological fluids is a procedure that has many applications in the field of prevention and treatment of COPD and related conditions. For example, the procedure can be used to: identify patients at risk of developing COPD; monitor the stage and/or progression of COPD in a patient; determine whether there is any regression of the disease state; evaluate the efficacy of prophylactic and therapeutic treatments for COPD (including use as biomarkers for intermediate end-points in the context of clinical trials); and assess the harmful effects of substances in causing COPD.

In preferred embodiments of these applications of the invention the analysis of nitroproteins follows the general protocol:

(i) obtain a sample of bronchoalveolar lavage fluid (BALF) from a patient;
(ii) immunoprecipitate the nitroproteins from the BALF sample with anti-nitrotyrosine antibodies;
(iii) digest the immunoprecipitated nitroproteins with a suitable protease to generate nitropeptides; and
(iv) analyse the nitropeptides by mass spectrometry and determine their sequence.

As appropriate, the presence and quantities of nitroprotein biomarkers in a test sample can be compared with a second sample. For instance, a negative control sample can be obtained from a non-smoking non-COPD patient. A positive control sample can be obtained from an individual who has been diagnosed with COPD. A second sample can also be derived from the same individual as the first test sample, but at a different time-point.

The nitroprotein biomarker may be undetectable in a negative control sample at the levels of detection made possible through use of the methodology described in detail below. Alternatively, the amounts of nitroprotein biomarker in the negative control sample may be significantly lower than in the test sample. For instance, the amounts of a specific nitroprotein marker in a negative control sample could be 10 times, preferably 100 times, more preferably 1000 times less than in a positive control sample. In order to make a positive prediction or diagnosis of COPD in a patient the amounts of specific nitroprotein biomarker in a sample from an individual should preferably be at least 10 times, more preferably at least 100 times, most preferably at least 1000 times greater than in a negative control sample.

In a preferred embodiment, the biological sample that is analysed for protein nitration is bronchoalveolar lavage fluid (BALF). BALF is obtained by washout of the alveolar compartment of the lung. This complex fluid contains cells and a wide variety of soluble components such as lipids, nucleic acids and proteins/peptides in low abundance. Other biological samples can be derived from lungs, such as tissue obtained from the lung (e.g. by surgery or biopsy), sputum, exhaled breath, exhaled breath condensates and nasal washings. Other non lung-derived biological samples include, for example: blood, plasma, serum, sweat, tears, urine, saliva, synovial fluid, cerebrospinal fluid (CSF), and body tissue other than from the lungs.

For identification and characterization of the proteins in the biological sample any appropriate state-of-the-art proteomics methods can be employed. In broad terms, nitroproteins from a biological sample can be isolated and separated at high resolution, for example by chromatography. The set of proteins can then be characterized using qualitative and quantitative techniques such as mass spectrometry. To facilitate identification and quantification the proteins can be digested to generate nitropeptides. The result is a nitroprotein or nitropeptide profile or "fingerprint". Thus, in any embodiment of the invention that comprises a step of identifying and/or quantifying a nitroprotein in a sample, it is possible as an alternative to carry out a proteolytic cleavage of the nitroprotein in the sample in order to identify and/or quantify nitropeptides instead.

The nitroproteins in the sample can be separated out by 2D polyacrylamide gel electrophoresis (2D PAGE), or nitropeptides by 2D liquid chromatography as described, for instance, in WO 2006/118522. Western blots carried out using anti-nitrotyrosine antibodies can be aligned with 2D PAGE gels enabling identification of immunopositive protein spots. These can then be excised, protease-digested, and the resulting peptides identified by conventional proteomics techniques, such as fingerprinting by MALDI mass spectrometry or capillary LC-MS/MS analyses. One drawback of this technique is that it is not well suited to detecting low levels of nitroproteins.

Conveniently, one step in characterization of the proteins in the biological sample is the enrichment of nitroproteins or nitropeptides from the sample. Biological samples such as BALF contain small amounts of protein, and nitroproteins represent only a tiny percentage of the total protein content (estimated at 0.0001%, as compared to an estimated 0.1% for phosphoproteins). Enrichment can be carried out utilizing antibodies of any type that are capable of selectively recognising and binding to nitrotyrosine residues. Antibodies of this type are known, can be easily prepared and are also commercially available. Antibodies can, for instance, be coupled to a support to generate a nitrotyrosine affinity column. Concentrating and preferentially enriching the nitroproteins from the sample in this way greatly facilitates subsequent identification of individual nitroproteins.

The concentrated/enriched nitroproteins in the sample can be proteolytically cleaved to generate nitropeptides to facilitate analysis. The nitropeptides can be separated by any conventional means such as liquid chromatography, but in a preferred embodiment, the nitropeptides are analyzed by mass spectrometry without the need for a prior separation step. Methods used in the technique of mass spectrometry are known to the skilled person and reviewed in Aebersold and Mann, Nature (2003): 56. Preferred ionisation methods are Electrospray Ionisation (ESI) and matrix-assisted laser desorption-ionization (MALDI, Hillenkamp et al. *Anal. Chem.*, 1991, 63:1193). According to the present invention matrix-assisted laser desorption/ionization (MALDI)-tandem mass spectrometry (MS/MS) is a preferred method for analyzing nitroproteins/nitropeptides. An alternative method is liquid chromatography tandem mass spectrometry (LC-MS/MS).

The nitropeptide sequences identified by mass spectrometry can then be compared with sequences in publicly accessible databases, for instance by accessing the SwissProt and TrEMBL Databases (collectively UniProt) through the BLASTP portal. Peptide sequence matches allow the skilled person to deduce from which protein the corresponding nitropeptide sequence originated. Methods of alignment of sequences for comparison are well known in the art. Altschul et al. (*Nature Genetics*, 6:119, 1994) presents a detailed consideration of sequence alignment methods and homology calculations.

Although MALDI-MS/MS is a very sophisticated and useful tool for peptide sequencing, it has technical limitations, and it is possible for sequencing errors to occur for various reasons. Because of this there may not always be a 100% match with the human source protein sequence. The very low abundance of a nitroprotein makes it more difficult to interpret the spectra accurately, and software used for analysis of MS spectra may fail to correctly assign the molecular peaks. It is necessary to accumulate hundreds of individual tandem mass spectra to obtain high quality product-ion spectra that are manually interpreted, to improve the signal-to-noise ratio of ions, to obtain clear b- and y-ions, and to provide a high level of confidence in the amino acid sequence that derives from the product ion spectrum. In spite of potential sequence errors, standard software homology analysis will allow the skilled person to deduce from which human homologue sequence the sequenced peptide is derived.

A particularly preferred embodiment of the invention provides a method for identifying a patient at risk of developing COPD, comprising the steps of:

(i) obtaining a sample of bronchoalveolar lavage fluid (BALF) from a patient;

(ii) immunoprecipitating the nitroproteins from the BALF sample with anti-nitrotyrosine antibodies;

(iii) digesting the immunoprecipitated nitroproteins with a suitable protease to generate nitropeptides;

(iv) analysing the nitropeptides by mass spectrometry and determining their sequence; and (v) identifying the patient as being at risk of developing COPD if one or more nitropeptides matches a fragment of the amino acid sequence of proteins selected from the group consisting of: progestin and adipoQ receptor family member III, zinc finger protein 432, proteasome subunit alpha type 2, NADH-ubiquinone oxidoreductase B14, slit homolog 1 protein, and lysozyme.

In accordance with the present invention, an "isolated" protein or peptide means one that has been removed from its naturally occurring environment, and includes proteins and peptides produced by recombinant DNA technology and chemically synthesized analogues.

The terms "nitroprotein" and "nitrated protein" are used interchangeably to refer to a protein in which one or more tyrosine residues has been modified by nitration to generate a 3-nitrotyrosine residue. A "peptide" is any fragment of a protein consisting of 2 or more amino acids. A peptide can be formed by enzymatic or chemical cleavage. Hundreds of suitable eukaryotic and prokaryotic proteolytic enzymes exist, and can be classified into the major groups of serine proteases, threonine proteases, cysteine proteases, aspartic acid proteases, metalloproteases and glutamic acid proteases. In a preferred embodiment trypsin, or another serine protease such as chymotrypsin or elastase, is used to digest nitroproteins from a biological sample, so preferred peptides of the invention are tryptic peptides of nitroproteins. Chemical proteolytic cleavage can be carried out using commercially available reagents such as cyanogen bromide or acids.

A "subfragment of a peptide" means a section of the full-length peptide which is at least 1 amino acid shorter than the full-length peptide. In particular a subfragment may be shorter than the full-length peptide, by 1, 2, or 3 amino acids at the N-terminus and/or the C-terminus (independently).

The terms "nitropeptide" and "nitrated peptide" are used interchangeably and can either refer to a peptide in which one or more tyrosine residues has been modified by nitration to form a 3-nitrotyrosine residue, or can refer to a peptide fragment of a nitroprotein (whether the peptide itself includes any nitrated tyrosine residues or not).

As used to refer to proteins or peptides, the term "homologous" is meant to indicate two proteins or peptides that share a majority of their amino acid sequences. Generally, homologous means having a sequence identity of at least 70%, more preferably at least 80%, even more preferably at least 90% and most preferably more than about 95% (counted over the full length alignment using NBCI Blast, gapped blastp set to default parameters). Homology for peptides or proteins is typically measured using standard sequence analysis software.

Quantification of total nitroprotein content in a sample can be carried out by immunoprecipitation using antibodies selectively recognizing 3-nitrotyrosine.

Quantification of protein or peptide level in a sample may be achieved using any techniques known to those skilled in the art, including but not limiting to quantitative mass spectrometry, enzyme-linked immunosorbent assays (ELISA), radioimmunoassays (RIA), immunoblotting assays (e.g. Western blot), immunofluorescent assays, immunoprecipitation assays, chemiluminescent assays, and immunohistochemical assays. Identification of specific individual nitroproteins can involve detection of the specific proteins within the nitroprotein immunoprecipitate (e.g. in a second step using another antibody specifically recognizing the protein). Alternatively, it may be possible to raise specific antibodies to the nitroprotein itself, capable of distinguishing the nitrated form from the non-nitrated form in BALF or other bodily fluids.

A preferred protein quantification technique is the ELISA technique (Engvall et al., (1971), *Immunochemistry*, 8:871-4; Stites et al., (1982) in *Basic and Clinical Immunochemistry*, 4th Edition, Chap. 22, Lange Medical Publications, Los Altos, Calif.; Reen, (1994), *Methods Mol. Biol.*, 32:461-6; which disclosures are incorporated by reference in their entireties). The ELISA assays embraced by the present invention may be, for example, of direct format (where the labelled first antibody reacts with the antigen, e.g., nitroprotein), of indirect format (where a labelled second antibody reacts with the first antibody that binds to the antigen), of competitive format (such as the addition of a labelled antigen), or of sandwich format (where both labelled and unlabelled antibodies are utilized), as well as of any other format one skilled in the art could envision.

The nitrated proteins found according to the Examples to be present in human ex-smoker BALF are:

Progestin and adipoQ receptor family member III/PAQR3 (Q6TCH7)

Zinc finger protein 432/ZNF432 (O948920)

Proteasome subunit alpha type 2 (P25787)

NADH-ubiquinone oxidoreductase B14 subunit/NDUFA6 (P56556)

Slit homolog 1 protein (rat homologue is O88279)

Lysozyme (ANOGA) (Q17005)

Aldose 1-epimerase (ACICA) (P05149)

PTS system lactose-specific EIICB component (STAAU) (P11162)

The Swiss-Prot accession numbers are given in brackets and the published full-length sequences are incorporated herein by reference.

Progestin and adipoQ receptor III (PAQR) is a multiple-pass protein and interacts with the ligand progesterone. Nitration occurred within the extra-membrane region and could interfere with receptor-ligand binding and signal transduction. It has previously been reported that Hormone Replacement Therapy including progesterone has positive effects on COPD symptoms.

Zinc finger protein 432, which is known to affect transcription regulation for a broad range of genes, was found to have been nitrated at a tyrosine residue within the KRAB (kruppel-associated box) domain that functions as a transcriptional suppressor, so it is conceivable that an effect of nitration would be to alter regulation of transcription within alveolar cells.

Proteasome subunit alpha type 2 is an important component of the proteasome complex. This complex is involved in protein synthesis, cancer formation, and lung fibrosis disease. The proteaseome subunit alpha type 2 is involved in the ATP-dependent ubiquitin-proteasome pathway, which is an important intracellular non-lysosomal proteolytic pathway. The ubiquitin-proteasome pathway is involved in the mechanisms of reduced contractile protein content in the diaphragms of patients with mild to moderate COPD (Ottenheijm et al. *Am. J. Respir. Crit. Care Med.*, 174: 997-1002; 2006).

NADH-ubiquinone oxidoreductase B14 is a component of mitochondrial complex I and of the mitochondrial membrane respiratory chain NADH dehydrogenase system, which is involved in the mechanisms of increased lung cell apoptosis and necrosis in COPD patients (Van der Toorn et al. *Am. J. Physiol. Lung Cell. Mol. Physiol.,* 292: L12211-L1218, 2007).

One of the nitropeptides derived from BALF protein displayed sequence identity with the rat Slit homolog 1 protein. For reasons already explained above, slight sequencing errors probably occurred and it is believed that the peptide was derived from the homologous human Slit homolog 1 protein rather than the rat version. Slit homolog 1 protein was found to have been nitrated in the EGF-like domain 3. Slit homolog 1 protein is normally secreted and functions as a ligand for the Roundabout (Robo) receptor-signalling pathway, which is implicated in neurogenesis, angiogenesis, and the immune response.

The closest matches to the lysozyme nitrated peptide are from arthropods. Currently it is unclear whether the peptides genuinely originated from an insect source or whether there could be another explanation for the fact that the peptide sequence does not closely match the human variant. Lysozyme is induced by bacterial infection, is expressed in salivary glands and tubules, and has primarily a bacteriolytic function. In tissues and body fluids lysozyme is associated with the monocyte-macrophage system and enhances the efficacy of immunoagents, and contributes to the antimicrobial defence of the alveolar lining layer (Shelley et al. *Biochem. Biophs. Acta,* 1096: 338-344, 1991) and respiratory system defence (Dajani et al. *Am. J. Respir. Cell Mol. Biol.,* 32: 548-552, 2005). Lysozyme was found to have been nitrated within the tyrosine kinase phosphorylation motif (K-y79wc-D-sg-Y85 (SEQ ID NO: 9)), which could interfere with its bacteriolytic function and inhibit the activity of immunoagents, which in humans could promote bronchoalveolar infection and inflammation.

Aldose 1-epimerase (mutarotase) was found to have been nitrated in a tyrosine kinase phosphorylation motif (K-fsl-D-gkt-$Y_{118}$ (SEQ ID NO: 10)). This is not a human protein but a bacterial protein normally involved in the interconversion of alpha- and beta-hexoses, which are essential for normal carbohydrate metabolism and the production of complex oligosaccharides. The peptide sequenced exactly matches the protein from *Acetinobacter baumannii*, a known nosocomial bacterial pathogen which causes ventilator-associated pneumonia.

One of the detected nitropeptides was derived from PTS system lactose-specific EIICB component. This is a bacterial protein normally involved in catalyzing the intake and phosphorylation of lactose, which is involved in sugar and energy metabolism. The peptide sequence was an exact match with the *Staphylococcus aureus* protein. *S. aureus* can have pathogenic effects in humans, including causing pneumonia.

It is interesting to note that two of the peptides identified by this novel methodology (PTS system lactose-specific EIICB component and aldose 1-epimerase) match peptide sequences from pathogenic bacteria, which—it is speculated—colonized the human patients who participated in the study. This observation is consistent with reports presented at the European Respiratory Society Annual Congress, 4-8 Oct. 2008 suggesting that analysis of the bacterial flora present in BALF allows diagnosis of specific bacterial lung infections, and that presence of pathogenic bacteria correlates with exacerbation of COPD symptoms (Kolosova K. et al. Abstract 2750: "The role of bacterial pathogens in exacerbation of COPD assessed by microbiological method and polymerase chain reaction"; Marin-Tapia A. et al. Abstract E255 "Characterization and effects of bronchial colonization and inflammation in stable COPD patients. PAC-COPD study"). At the same congress a poster was presented identifying potential BALF biomarker proteins for COPD (Mileo et al. "Comparative Proteomics of Bronchoalveolar Lavage Fluid Towards Biomarkers of COPD"). Among those proteins differentially expressed in COPD vs control patients were several bacterial proteins.

TABLE 1

SEQ ID Numbers of peptide sequences derived from nitroproteins in ex-smoker BALF.

| SEQ. ID NO. | Peptide Sequence | Protein Name |
|---|---|---|
| 1 | LYTY*EQIPGSLKDNPYITDGYRAYLPSR | Progestin and adipoQ receptor family member III |
| 2 | DLYRDVMLEIY*SNLLSMGYQVSKPDALSK | Zinc finger protein 432 |
| 3 | DY*LAAIA | Proteasome subunit alpha type 2 |
| 4 | ELY*RAWY*REVPNTVHQFQ#LDITVK | NADH-ubiquinone oxidoreductase B14 subunit |
| 5 | HDCVN#GGVCVDGIGNYTCQCPLQY*TGR | Slit homolog 1 protein |
| 6 | NKNGSTDYGIFQINN#KY*WCDSGYGSN#DCK | Lysozyme |
| 7 | FSLDGKTY*NLEKNNGPN#SLHSGN#PGFDK | Aldose 1-epimerase |
| 8 | EY*QLILAPQVASNY*EDIKQ#DTDR | PTS system lactose-specific EIICB component |

Wherein the amino acids are represented by their conventional single letter codes, and Y* refers to tyrosine residues that may be nitrated.
Q# refers to glutamine residues that may be deamidated (post-translational modification)
N# refers to asparagine residues that may be deamidated (post-translational modification)
In each case the residue preceding the N-terminal and C-terminal tryptic cleavage site is K or R.

The present invention encompasses the isolated peptides of SEQ IDs NO: 1-8 in their nitrated and non-nitrated forms, and sequences having at least 70% homology to those sequences (homologues), and subfragments of those sequences.

In one aspect of the invention there is provided use of any of the nitropeptides of SEQ ID NO. 1-8, or a homologue or a subfragment thereof, in the diagnosis of a precursor condition to COPD.

As defined herein a patient is a human or animal individual who is deemed to be at risk of developing COPD or who has already been diagnosed with the condition by spirometry or any other suitable diagnostic test.

Patients at risk of developing COPD are usually smokers or ex-smokers, or anyone exposed to polluted or toxic air. Smokers can be defined as individuals who habitually and actively inhale cigarette smoke from cigarettes or other delivery methods such as cigars and pipes. Passive smokers are individuals who do not themselves actively smoke, but who inhale smoke generated by others, in a confined space and/or in close proximity. Chronic smokers can be defined as active smokers who have habitually smoked for at least the preceding year, or at least the preceding 2 years, or 5 years, or 10 years. A heavy smoker can be defined as a smoker who habitually consumes more than 20 standard strength cigarettes per day. Ex-smokers can be defined as individuals who at one time habitually smoked, but who have rarely or never smoked a cigarette in the preceding year, preferably in the preceding 2 years, more preferably in the preceding 5 years, most preferably in the preceding 10 years.

As referred to herein, smoke is generally taken to mean smoke generated from burning tobacco. However, it can also refer to smoke generated from burning *cannabis* or any other substance.

In the broadest sense, the term COPD as used here refers to COPD itself and also its subconditions chronic bronchitis and emphysema.

The Global Initiative for Chronic Obstructive Lung Disease (GOLD) has classified 4 different stages of COPD. In one aspect, the invention provides means to prevent progression of COPD in a subject from one stage to a subsequent stage in the GOLD classification. In another aspect the invention allows monitoring of the progression of the disease from one stage to a subsequent stage in the GOLD classification.
GOLD Classification for COPD:

Stage 0: At Risk for COPD. Symptoms of chronic cough and sputum production may be present, but patients have normal spirometry readings.

Stage 1: Mild COPD. Characterized by $FEV^1>=80\%$, $FEV^1/FVC<70\%$. Patients may have or not have chronic cough and increased sputum production.

Stage 2: Moderate COPD. Characterized by a worsening of airflow ($30\%>=FEV^1>80\%$). Patients with stage-2 disease often are symptomatic, seek medical attention, and have shortness of breath with exertion. Stage 2 has 2 subcategories: IIA and IIB. IIA patients have a $FEV^1$ between 50% and 80%; stage IIB patient have a $FEV^1$ between 30% and 50%. Patients with $FEV^1$ below 50% are especially prone to acute exacerbations of disease.

Stage 3: Severe COPD. Characterized by an $FEV^1$ below 30%. Patients are also included in stage 3 if they have respiratory failure or right heart failure. The quality of life is severely affected in these patients. Acute exacerbations in this patient population often require hospitalization and are frequently life threatening.

Where $FEV^1$ means forced expiratory volume in 1 second and FVC is forced vital capacity.

As used herein, "early stage" COPD is intended to mean GOLD Stage 0 or a precursor condition thereto.

The identification of characteristic nitroprotein or nitropeptide fingerprints in patients at risk of developing COPD also allows the skilled person to create novel therapies to help prevent development or progression of that disease. When screening for a therapeutic agent capable of treatment of COPD, it is preferable that the amount of total nitroprotein in the sample, or the amount of a specific individual nitroprotein or nitropeptide in the sample post-administration of the therapeutic agent is reduced at least 2-fold, preferably at least 5 fold, more preferably at least 10 fold relative to the pre-administration sample.

Knowledge of the nitroprotein biomarkers disclosed herein permits the development of therapies that can selectively target the nitroproteins so as to inactivate, neutralize, clear or degrade those proteins to ensure their malfunction as a consequence of nitration does not have any biological repercussions.

For example, ligands which are capable of specifically binding these nitroproteins or nitropeptides can be used therapeutically and prophylactically for COPD. Ligands can include antibodies (polyclonal or monoclonal), antibody fragments, proteins, protein domains, peptides, small molecules, and aptamers (protein or nucleic acid).

Anti-nitroprotein/-nitropeptide antibodies may be prepared by any suitable method known in the art. Polyclonal antibodies may be prepared using an intact nitroprotein or fragments thereof as the immunogen. As will be appreciated by those having skill in the art, the immunogen can be conjugated to a carrier protein, if desired or necessary (e.g. if the ligand is <5 kDa), to increase immunogenicity. Commonly used carriers that are routinely chemically coupled to peptides include but are not limited to bovine serum albumins, thyroglobulin, hemocyanin and tetanus toxoid. The coupled immunogen-carrier is then used to immunize a recipient animal (e.g., mouse, rat, sheep, goat, or rabbit) and polyclonal antibodies are isolated from said immunized animal, preferably from the serum of said animal.

As used herein, the term "monoclonal antibody" is not limited to antibodies produced through hybridoma technology but it rather refers to an antibody that is derived from a single clone, such as a eukaryotic cell, prokaryotic cell, or phage clone. Monoclonal anti-nitrated protein antibodies may be prepared by any conventional methods, including isolation from splenic cells of an immunized animal, hybridoma, genetically engineered monoclonal antibody or antibodies fragments or antibody produced by in vitro immunization by certain cells, and by phage display techniques. For example, see Kohler, et al., *Nature*, 256:495, 1975; *Current Protocols in Molecular Biology; Harlow and Lane, Antibodies: A Laboratory Manual*, Cold Spring Harbor Laboratory, New York (1988); Hammerling, et al, (1981) *Monoclonal Antibodies and T Cell Hybridomas*, Elsevier, N.Y. 563-681) (said references incorporated by reference in their entireties).

Antibodies may be made by recombinant DNA techniques or synthetic chemistry. The term recombinant antibody is intended to include all antibodies that are prepared, expressed, created or isolated by recombinant means, such as antibodies expressed using a recombinant expression vector transfected into a host cell; antibodies isolated from a recombinant, combinatorial antibody library; antibodies isolated from an animal (e.g. a mouse) that is transgenic for human immunoglobulin genes; or antibodies prepared, expressed, created or isolated by any other means that involves splicing of human immunoglobulin gene sequences to other DNA sequences. Such recombinant antibodies include humanised, CDR grafted, chimeric, deimmunised and in vitro generated antibodies.

"Antibody fragments" comprise a portion of an intact full-length antibody, preferably the antigen binding or variable region of the intact antibody. Examples of antibody fragments include Fab, Fab', F(ab')2, and Fv fragments; diabodies; linear antibodies (Zapata et al., Protein Eng., 8(10):1057-1062 (1995)); single-chain antibody molecules; and multispecific antibodies formed from antibody fragments. Antibody fragments may be produced, for example, from hybridoma-produced antibodies by proteolytic cleavage, using enzymes such as papain (to produce Fab fragments) or pepsin (to produce F(ab')2 fragments) or other proteases.

Ligands with desired parameters can be selected from large combinatorial libraries of biopolymers using instrumental separation techniques with well-described kinetic behaviour, such as Kinetic capillary electrophoresis (KCE), Surface Plasmon resonance (SPR) etc. Ligands bind specifically to their targets, i.e. they have a particular affinity to their targets due to their respective conformations and molecular interactions. In one embodiment they also bind selectively to their nitrated targets, i.e. they have at least 5-fold, preferably at least 10-fold, more preferably at least 50-fold, even more preferably at least 100 fold, and ideally at least 1000-fold greater affinity for the nitrated form over the non-nitrated form.

The ligands of the invention are optionally coupled with moieties which are capable of directing destruction of the target nitroprotein itself (e.g. through ubiquitin conjugation and destruction in the proteasome) or the cell in which that nitroprotein is situated, for instance by apoptosis.

The ability of the ligands of the invention to selectively target a nitrated protein versus its non-nitrated form can be assessed and confirmed by in vitro assays such as ELISA.

Knowing that specific proteins with critical roles have been irreversibly modified by nitration also leads to the possibility of developing a prophylactic or therapeutic vaccine based on the nitroprotein (or a nitropeptide fragment thereof). Through administration of the nitroprotein or nitropeptide as a vaccine the body is induced to raise an immune response against the damaged, nitroprotein in situ, thereby eliminating any undesirable physiological effects as a result of the nitration. Thus in another aspect, the invention provides vaccine compositions comprising one or more of the nitroproteins or nitropeptides of the invention, in conjunction with one or more pharmaceutically acceptable excipients or carriers.

Preferably, the vaccine compositions of the invention comprise one or more conventional adjuvants. Examples of adjuvants are: mineral salts, e.g., aluminium hydroxide and aluminium or calcium phosphate gels; oOil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion); particulate adjuvants, e.g., virosomes (unilamellar liposomal vehicles incorporating influenza haemagglutinin), AS04 ([SBAS4] A1 salt with MPL), ISCOMS (structured complex of saponins and lipids), polylactide co-glycolide (PLG); microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array); and inert vehicles, such as gold particles.

The pharmaceutical and vaccine compositions of the invention can be formulated to be administered by any convenient route, such as oral, intramuscular, intravenous, subcutaneous, rectal, vaginal, inhalational, intranasal, transdermal etc. Suitable dosage forms include all those known to the skilled person, such as tablets, capsules, powders, sustained release formulations, ointments, gels, creams, suppositories, eye drops, transdermal patches, syrups, solutions, suspensions, aerosols, solutions for nebulizers, nasal sprays etc. In a preferred embodiment the composition is formulated for delivery by the inhalation or intranasal routes, for instance in an aerosol or a nasal spray.

Pharmaceutical compositions according to the invention comprise one or more pharmaceutical carriers or excipients. Suitable pharmaceutical carriers include inert diluents or fillers, water, saline and various organic solvents. The pharmaceutical compositions may, if desired, comprise additional ingredients such as flavorings, binders, excipients, disintegrants, suspending agents, lubricants, glidants, sweeteners, flavoring agents, coloring agents and the like. Detailed information on suitable excipients can be found in the *Handbook of Pharmaceutical Excipients*, Pharmaceutical Press, 5th Ed. 2006.

The pharmaceutical and vaccine compositions of the invention may further comprise one or more additional active substances. In particular, it may be desirable to incorporate one or more medicaments conventionally prescribed to patients with lung disease, such as corticosteroids, bronchodilators, vaccines against pneumococcus and influenza, mucolytics, antibiotics and antiinflammatories.

The precise dosage of active substance in the pharmaceutical and vaccine compositions can easily be determined and optimised by a person skilled in the art.

In another aspect, the present invention relates to diagnostic kits for COPD comprising reagents capable of identifying and quantifying individual nitroproteins or nitropeptides, wherein those nitroproteins and nitropeptides are preferably selected from the group of nitrated proteins consisting of: progestin and adipoQ receptor family member III; zinc finger protein 432; proteasome subunit alpha type 2; NADH-ubiquinone oxidoreductase B14; slit homolog 1 protein; lysozyme; aldose 1-epimerase; PTS system lactose-specific EIICB component; and peptide fragments thereof. In one embodiment, said kit comprises an antibody able to bind specifically to a nitroprotein or nitropeptide fragment thereof. In another embodiment, said antibody is labelled. Optionally said kit comprises the reagents necessary for performing an ELISA.

Other features of the invention will become apparent in the course of the following descriptions of exemplary embodiments which are given for illustration of the invention and are not intended to be limiting thereof.

EXAMPLES

BALF Collection

Bronchoalveolar lavage was performed by clinicians. Five separate 30 ml aliquots of 0.9% sterile saline were instilled into the right middle lobe or lingula. BALF samples were collected, aliquoted into polypropylene tubes, and stored at −80° C. prior to further analyses. A 5 ml aliquot was reserved for proteomics analysis.

BALF Protein Preparation.

Two separate 5 ml BALF samples (male, ex-smoker without COPD, 56 and 66 year old) were vacuum-dried (0° C.), and the residues were redissolved in 180 µl of Pierce M-PER protein extraction buffer. The solutions were centrifuged at 15000 g for 30 minutes, and the supernatants of the two samples were combined (about 350 µl) for nitrotyrosine immunoaffinity analysis.

Nitroprotein Immunoprecipitation.

Nitrotyrosine immunoprecipitations were performed as described in Zhan et al. *Anal. Biochem.*, 354: 279-289, 2006 (incorporated herein by reference in its entirety). Briefly, rabbit anti-nitrotyrosine polyclonal antibody (92 µg, Chemicon International, Temecula, Calif., USA) was coupled with immunopure immobilized protein G beads (400 µl, Pierce) for 2 hours with gentle shaking in buffer (0.14M NaCl, 0.008M sodium phosphate, 0.002M potassium phosphate, and 0.01M KCl; pH 7.4), and washed to remove any unbound antibody (Pierce Immunoprecipitation kit, product 45225). The bound antibody was covalently crosslinked to protein G with gentle shaking (40 minutes) in disuccinimidyl suberate (final concentration 0.0025%); the beads were washed briefly with a low pH buffer (pH 2.8) to remove non-crosslinked antibody, and re-equilibrated into the above binding buffer. The immobilized anti-nitrotyrosine antibody (about 92 µg) was packed into a column and then incubated overnight at 4° C. with the prepared BALF protein samples to capture the nitrotyrosine-containing proteins; the column was washed 3 times with the binding buffer (400 µl) and the nitrated proteins were eluted with Pierce elution buffer into a volume of about 250 µl.

Tryptic Peptide Preparation.

An aliquot (20 µl) of immunoprecipitated (IP) products was treated with 1 µl of 1M Tris (pH 9.5). Sequencing grade-modified trypsin (20 µg, Promega, Madison, Wis., USA) was dissolved in a volume of solution (100 µl, pH 8.2) that consisted of 5 µl trypsin resuspension buffer that contained 50 mM acetic acid (pH 2.8) and 95 µl of 200 mM $NH_4HCO_3$ (pH 8.2). The enzyme digestion reaction system (100 µl, final concentration of $NH_4HCO_3$=50 mM, pH 8.1), which consisted of 21 µl neutralized IP products, 25 µl trypsin solution, and 54 µl $ddH_2O$, was incubated overnight at 37° C. An aliquot (20 µl) of the tryptic peptide mixture was purified with a Millipore ZipTip C18 column according to the manufacturer's instructions (Millipore, Billerica, Mass., USA). The purified tryptic peptides were eluted directly from the microcolumn onto a vMALDI plate with 2 µl of an α-cyano-4-hydroxycinnamic acid (CHCA) solution (2.5 mg/ml CHCA in 50% v/v acetonitrile/0.1% v/v trifluoroacetic acid); that solution was dried in ambient air for mass spectrometry (MS) analysis.

Protein Identification with MALDI-Tandem Mass Spectrometry.

The tryptic peptides were analyzed with a vMALDI-LTQ tandem mass spectrometer in the "Nth-order double play" data-dependent experimental mode to obtain the amino acid sequence of each peptide (as described in Zhan et al.). Briefly, the crystal-positioning system (CPS) and auto spectrum filter (ASF; threshold=500 counts for an MS scan and 250 counts for an $MS^2$ scan) were enabled for the vMALDI source. The automatic gain control (AGC) was enabled to automatically adjust the number of laser shots to maintain the quality of the spectra. For an MS scan, high-mass range (m/z 600-4000), normal scan rate, full scan, polarity, profile data type, and five microscans of each experiment were used. For an $MS^2$ scan, the 50 most intense peaks in the full MS spectrum, high-mass range (m/z 50-4000), normal scan rate, polarity, centriod data type, isolation width 3.0 Th, normalized collision energy 40 (arbitrary units), default charge state 1, minimal signal threshold 100 counts, activation Q value 0.25, activation time 30 ms, and five microscans of each experiment were used. Instrument operation and data acquisition utilized the Xcalibur software package (ThermoFinnigan). Initial protein identifications from MS/MS data utilized the Bioworks TurboSequest software search engine (ThermoFinnigan, version 3.2) and the Swiss-Prot protein database. The Swiss-Prot database search parameters included 2 allowed missed tryptic cleavage sites, precursor-ion mass tolerance=2 Da, fragment-ion mass tolerance=1.0 Da, and protein modifications for Tyr nitration (+45 mass unit), Asn and Gln deamidation (+1 mass unit), and Met oxidation (+16 mass unit). Each nitrotyrosine-containing peptide was examined manually, as described in Zhan et al. The residue that preceded the N-terminus or C-terminus must be K or R with singly charged b-, y-, and a-ion series for a nitrotyrosine-positive search result. An accumulated $MS^2$ spectrum (n=50-100 scans) of each nitrotyrosine-positive search result was acquired on the vMALDI-LTQ Tune page to improve the signal-to-noise (S/N) ratio, and was used to search the Swiss-Prot database with Bioworks 3.2 to corroborate each positive search result.

Furthermore, most of the prominent peak within the MS spectrum was selected to directly acquire the accumulated (n=50) $MS^2$ spectrum whether it was a nitropeptide or not. The MS/MS data were used to identify the protein and nitrotyrosine site as described above. NCBI BLASTP (version 2.2.17; http://ca.expasy.org/cgi-bin/blast.pl) was used to determine the identity of each nitropeptide that was aligned to a protein in the UniProtKB database (6,489 sequences that consist of Swiss-Prot and TrEMBL sequences; Jul. 1, 2008).

Protein Domain and Pathway Analyses.

Protein domain and motif analyses were carried out with ScanProsite (http://us.expasy.org/tools/scanprosite/), and Motifscan (http://myhits.isb-sib.ch/cgi-bin/motif scan). Each nitrotyrosine site was located within the corresponding protein domain and motif. The pathway networks that could involved the nitroproteins were analyzed with Ingenuity Pathways Analysis software (Ingenuity® Systems, www.ingenuity.com)

Results.

MS/MS data provided the amino acid sequences of nitrotyrosine-containing peptides from human ex-smoker BALF, provided in Table 1.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for identifying a smoker or an ex-smoker human being at risk of developing chronic obstructive pulmonary disease (COPD), comprising:
   (i) obtaining from said human being a biological sample in which one or more nitroproteins result from an inflammatory response in the lung causing formation of nitric oxide (NO) free radical which reacts with superoxide anion ($O_2^-$) to form nitrosant peroxynitrite anion ($ONOO^-$) which causes addition of nitrite ($NO_2$) to protein tyrosine residues;
   (ii) conducting proteolytic cleavage of said one or more nitroproteins in said sample with a suitable protease to generate nitropeptides;

(iii) selectively identifying the presence or absence of the nitropeptide of SEQ ID 1 in said sample; and
(iv) identifying the patient as being at risk of developing COPD if said nitropeptide of SEQ ID 1 is present in the sample.

2. A method according to claim 1, wherein said biological sample is a sample of bronchoalveolar fluid or a sample derived from the lung.

3. A method according to claim 1, which comprises identifying said nitropeptide of SEQ ID 1 by mass spectrometry.

4. A method according to claim 3, wherein said mass spectrometry is matrix-assisted laser desorption/ionization (MALDI)-tandem mass spectrometry.

5. A method according to claim 1, wherein said biological sample is a sample of bronchoalveolar lavage fluid.

6. A method according to claim 1, wherein said biological sample is a sample of sputum.

7. A method according to claim 1, wherein said biological sample is a sample of exhaled breath.

8. A method according to claim 1, wherein said biological sample is a sample of exhaled breath condensate.

9. A method according to claim 1, wherein said biological sample is a sample of a nasal washing.

* * * * *